US00PP29620P2

(12) United States Plant Patent
Piroche

(10) Patent No.: US PP29,620 P2
(45) Date of Patent: Aug. 21, 2018

(54) ***BERGENIA* PLANT NAMED 'MERRY BELLS'**

(50) Latin Name: *Bergenia omeiensis*
Varietal Denomination: Merry Bells

(71) Applicant: Pierre Piroche, Pitt Meadows (CA)

(72) Inventor: Pierre Piroche, Pitt Meadows (CA)

( * ) Notice: Subject to any disclaimer, the term of this patent is extended or adjusted under 35 U.S.C. 154(b) by 0 days.

(21) Appl. No.: 15/530,776

(22) Filed: Feb. 27, 2017

(51) Int. Cl.
*A01H 5/02* (2018.01)

(52) U.S. Cl.
USPC ..... Plt./409

(58) Field of Classification Search
USPC ..... Plt./409
CPC ..... A01H 5/02; A01H 5/00; A01H 6/80
See application file for complete search history.

(56) References Cited

PUBLICATIONS

Lascelle. Issuu. Pierre's three new Camellias, Maple Ridge News Mar. 25, 2016, retrieved on Mar. 12, 2018, retrieved from the Internet at https://issuu.com/blackpress/docs/i20160325074535760, p. 21. (Year: 2016).*

* cited by examiner

*Primary Examiner* — June Hwu
(74) *Attorney, Agent, or Firm* — Bethany R. Roahrig; Barbara Campbell; Cochran Freund & Young LLC

(57) ABSTRACT

A new cultivar of *Bergenia omeiensis* named 'Merry Bells' that is characterized by compact, low-growing plant habit, small rounded glossy green leaves which lie almost horizontal and clusters of white and soft pink bell-shaped flowers held on orange-red stems. The flowers of 'Merry Bells' emerge outward-facing and then gently recurve to expose orange-red calyces. In combination these traits set 'Merry Bells' apart from all other varieties of *Bergenia* known to the inventor.

3 Drawing Sheets

Genus and species: *Bergenia omeiensis.*
Variety denomination: 'Merry Bells'.

BACKGROUND OF THE NEW PLANT

The present invention relates to a new and distinct cultivar of *Bergenia* which is grown as an ornamental plant for use in containers and in the landscape. The new cultivar is known botanically as *Bergenia omeiensis* will be hereinafter referred to by the denomination 'Merry Bells'.

In 1999, the inventor collected and sowed seeds from an open-pollination of unpatented and unnamed selected maternal plants which exhibited tidy plant habits and contrasting colors in their flowers and stems. The resulting seedlings, approximately 200, were transplanted into containers in spring 2000 and maintained in a frost-protected greenhouse for evaluation during 2000, of which 118 plants were set aside for further observation during spring 2001.

In 2001, 'Merry Bells' was selected from a large population of unnamed and unreleased seedling parents for its unique combination of smaller size, smaller leaves which lie almost horizontal, and its delicate white and soft pink flowers which are carried on unusually short stems. Successive cycles of multiplication were conducted in the inventor's tissue culture laboratory in Pitt Meadows, British Columbia, Canada from 2001 until March 2016. The tissue culture process commenced with initiation of plant meristems. Thereafter, multiplication proceeded by basal division (excision and rooting of discrete basal shoots). The inventor removed and grew to flowering some plants from each cycle of multiplication and has determined that 'Merry Bells' is stable and reproduces true to type in each successive generation. 'Merry Bells' has not been sold or made publicly available more than one year prior to the filing date of the instant application.

SUMMARY

The following traits have been repeatedly observed and represent the distinguishing characteristics of the new *Bergenia* cultivar 'Merry Bells'. These traits in combination set 'Merry Bells' apart from all other existing varieties of *Bergenia* known to the inventor. 'Merry Bells' has not been tested under all possible conditions and phenotypic differences may be observed with variations in environmental, climatic and cultural conditions, however, without any variance in genotype.

1. 'Merry Bells' exhibits a compact, low-growing plant habit.
2. 'Merry Bells' exhibits small rounded glossy green leaves which lie almost horizontal.
3. Under cool conditions in early spring, the margins of the leaves of 'Merry Bells', and occasional parts of the leaf blade develop a bronzed appearance.
4. 'Merry Bells' exhibits clusters of bell-shaped flowers held on orange-red stems.
5. The flowers of 'Merry Bells' emerge outward-facing and then gently recurve to expose orange-red calyces.
6. The opening flowers of 'Merry Bells' are pure white in color.
7. As the flowers of 'Merry Bells' mature to become fully open, the inner surfaces of the corolla tube and the bases of the petals increasingly develop pink coloration, and the stamens develop a deep pink-red coloration.

8. The outer surfaces of the flowers of 'Merry Bells' remain pure white at all stages of development.
9. 'Merry Bells' flowers from early spring until early summer.
10. After 1 year of growth in a 9 cm container, a plant of 'Merry Bells' is 10 cm in height and 15 cm in width.
11. After 2 to 3 years of growth in a 1 gallon container, a plant of 'Merry Bells' is 20 cm in height and 20 cm to 30 cm in width.
12. 'Merry Bells' may be propagated by division, by leaf-stem cuttings and by tissue culture.
13. 'Merry Bells' is hardy in USDA Zone 6.

BRIEF DESCRIPTION OF THE PHOTOGRAPHS

The accompanying color photographs illustrate the overall appearance of the new *Bergenia* variety 'Merry Bells' showing colors as true as it is reasonably possible to obtain in colored reproductions of this type. Colors in the photographs may differ from the color values cited in the detailed botanical description, which accurately describe the actual colors of the new variety 'Merry Bells'. All photographs are of one year old plants of 'Merry Bells' which were grown in 9 cm containers outdoors at the inventor's nursery in Pitt Meadows, British Columbia, Canada.

FIG. 2 illustrates the pure white color of the outer surfaces of the petals and the contrasting orange-red calyx, sepals and peduncle of 'Merry Bells'.

Figure 1:
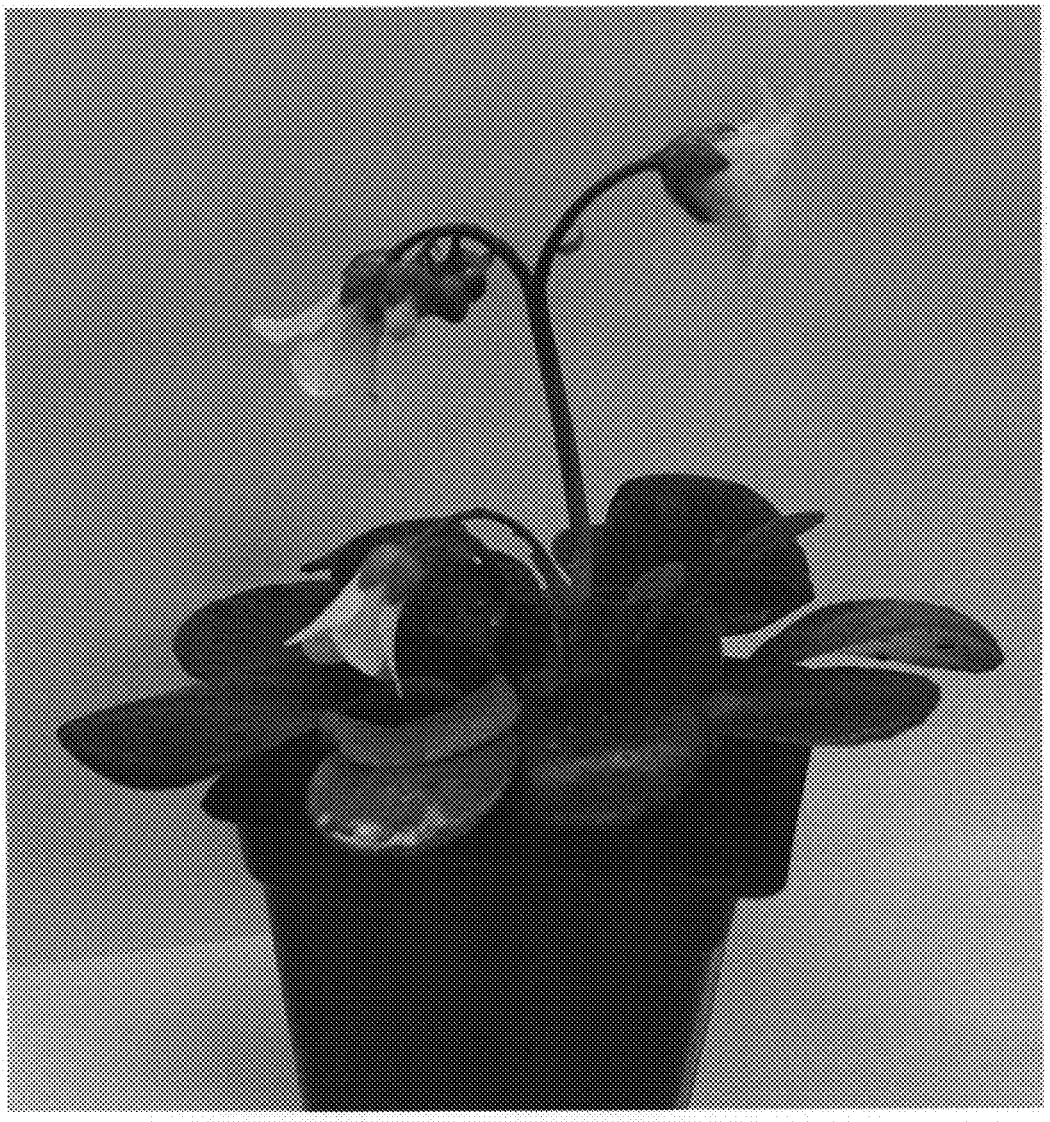
FIG. 1 depicts a one year old plant of 'Merry Bells' when first flowering in spring.
Figure 2:
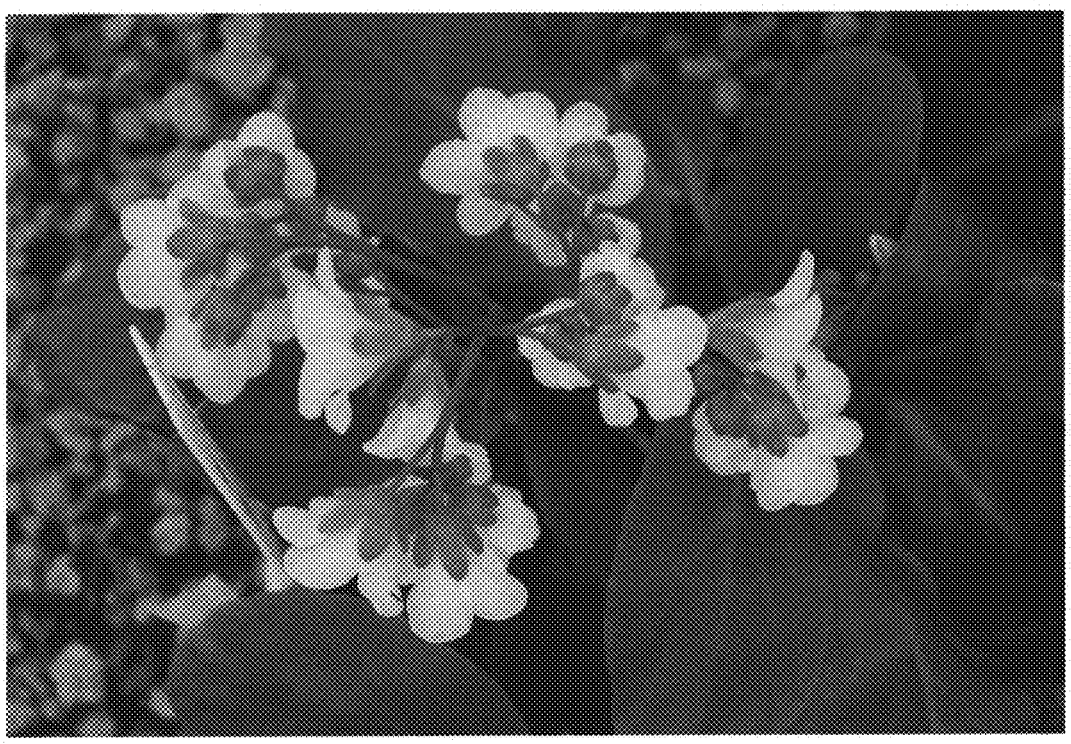
FIG. 2 depicts the typical recurved inflorescence of 'Merry Bells' in early summer.
Figure 3:
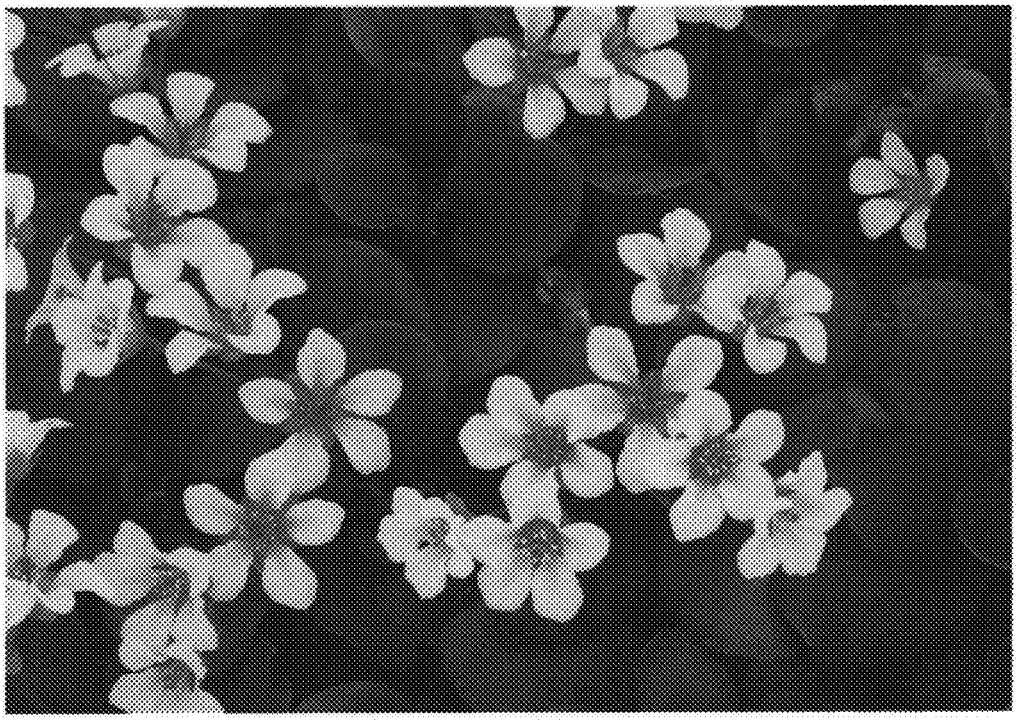

FIG. 3 depicts the typical white and pink colors of the inner surfaces of the corolla tube and the petals as the flowers develop and open fully. This photograph was taken at first flowering at the end of March. The plant illustrated was growing in a cool (frost-protected) greenhouse in Pitt Meadows, British Columbia.

The photographs were made using conventional techniques and although flower and foliage color may appear different from actual color due to light reflectance, they are as accurate as possible by conventional photography.

BOTANICAL DESCRIPTION OF THE PLANT

The following is a detailed botanical description of 'Merry Bells'. Data was collected in Pitt Meadows, British Columbia, Canada from two year old plants grown outdoors and in a greenhouse. Color determinations are made in accordance with the 2001 edition of The Royal Horticultural Society Colour Chart, London, England, except where general color terms of ordinary dictionary significance are used. The growing requirements of 'Merry Bells' are similar to the species *Bergenia omeiensis.*

Botanical classification:

*Genus.*—*Bergenia.*

*Species.*—*omeiensis.*

*Variety.*—'Merry Bells'.

Parentage: Successive open pollinations of plants and seedlings of *Bergenia omeiensis* raised by the inventor.

Plant description:

*Commercial classification.*—Hardy herbaceous perennial.

*Use.*—For use in containers, and in the landscape as a border plant or as a groundcover.

*Bloom period.*—Early spring to early summer (late March to June in British Columbia, Canada).

*Plant habit.*—Clumping, low growing. Leaves flat and layered, close to horizontal.

*Vigor.*—Moderate.

*Dimensions.*—After one year of growth: 15 cm in width, 10 cm in height. At maturity in the landscape: 20 cm to 30 cm in width, 20 cm in height.

*Hardiness.*—USDA Zone 6.

Propagation requirements: Propagation may be carried out any time of year using division or leaf cuttings (stems attached) or tissue culture. Rooting is promoted by bottom heat from October to March. The inventor has observed that rooting hormone is beneficial, specifically if cuttings are quickly dipped in a 1,000 to 2,000 parts per million solution of indole-3-butyric acid (IBA compound). Under these conditions, newly propagated plants of 'Merry Bells' will be fully rooted in a 9 cm container in 4 to 5 weeks. In order to propagate 'Merry Bells' by tissue culture, meristems of the initial plant must be initiated to produce new plants on their own roots in vitro. Thereafter, multiplication of 'Merry Bells' may proceed by division or excision of descrete basal shoots, which are established on their own roots in vitro.

*Root system.*—Fibrous.

Cultural requirements: 'Merry Bells' prefers well-drained garden soil or a container potting medium consisting of one-third peat, one-third fine perlite and one-third coarse perlite. Plants of 'Merry Bells' may be fertilized using slow-release fertilizer once per year or liquid fertilizer several times during the growing season. 'Merry Bells' will be fully rooted and will flower in a 15 cm or 1 gallon container after approximately 10 to 12 weeks from transplanting a 9 cm container-grown plant.

Foliage:

*Type.*—Simple.

*Arrangement.*—Alternate.

*Shape.*—Obovate to orbicular.

*Apex.*—Rounded.

*Base.*—Cuneate.

*Margin.*—Predominantly entire. Leaves which are not yet fully expanded bear tiny ovoid glandular nodes around the margin at intervals, approximately 0.5 cm apart. Nodes protrude from the margin by approximately 0.5 mm, giving the appearance of small teeth.

*Leaf margin glandular node color.*—Ranges between 185A and 171B.

*Surface, texture.*—Leathery, glabrous.

*Leaf dimensions.*—5 cm to 7 cm in length, up to 5 cm in width.

*Leaf color* (*except cold conditions*).—141C (adaxial surface); 141A (abaxial surface).

*Leaf color* (*early spring, cold conditions*).—Ranges between 135B and 136B on both surfaces with a margin color of 185A.

*Venation.*—Pinnate.

*Vein color.*—As leaf blade except midrib lighter 141D (both surfaces) in warm temperatures, 185A in cold conditions.

*Attachment.*—Petiolate.

*Petiole dimensions.*—8 mm to 15 mm in length and 4 mm in diameter.

*Petiole surface.*—Glabrous.

*Petiole shape*.—Cylindrical.

*Petiole color*.—60A.

Inflorescence and flowers:

*Inflorescence type*.—Scorpioid cyme consisting of initial single recurved terminal flower followed by recurved cluster of flowers.

*Number of cymes*.—Initially (first flowering) 1 to 2, increasing to 3 to 5.

*Number of flowers per scape*.—(Fully developed): 8 to 12.

*Inflorescence dimensions*.—Approximately 10 cm spread overall.

*Peduncle*.—Dimensions: 12 cm in length, 3 mm in diameter. Shape, surface: Cylindrical, glabrous. Color: 180B.

*Buds* (*immediately prior to opening*).—Dimensions: 12 mm in length, 8 mm in diameter. Shape: Ellipsoid. Color: 178B. Surface: Smooth, glossy.

*Flowers*.—Shape: Campanulate. Aspect: Downward facing. Petals: Five in number, unfused, overlapping until fully open. Dimensions: 18 mm in length, 13 mm in width. Petal shape: Obovate, apex rounded, base attenuate. Surface: Smooth, glossy. Color (adaxial surface): Predominantly pure bright white (whiter than NN155D) except pink N155C becoming N66C towards base, and red-purple N66B at base when flower fully open and petals are entirely separated. Color (abaxial surface): Pure bright white (whiter than NN155D). Calyx, sepals: Campanulate, five flared sepals fused at base. Sepal dimensions: 8 mm in length (from fused base), 4 mm in width. Sepal shape: Oblanceolate. Sepal surface: Smooth, waxy. Sepal color (both surfaces): 180C. Lastingness of the inflorescence and individual flowers: The typical interval between the opening of the first flower in the scape and the last fully open flower is 3 to 4 weeks.

*Pedicel*.—Dimensions: 5 mm to 10 mm in length, 2 mm to 3 mm in diameter. Shape, surface: Cylindrical, glabrous. Color: 180C.

Reproductive organs:

*Filaments*.—10, length 13 mm, color white NN155D when flowers newly open, becoming red-purple N66B when flower fully open.

*Anthers*.—Ellipsoid, color NN155D, length 0.5 mm.

*Style*.—3, fused longitudinally, length 15 mm, color N34A.

*Stigma bilobed, color*.—144B.

*Pollen*.—Moderate amount, color, 4C.

*Ovary*.—Ovoid, partly inferior.

Fruit and seed: None observed to date.

Diseases and pests: Except for incidence of common aphids, no pests or diseases have been observed to affect 'Merry Bells'.

COMPARISON WITH KNOWN VARIETY

A common variety of *Bergenia* in commerce is *Bergenia* 'Bressingham Ruby' (U.S. Plant Pat. No. 7,344). 'Bressingham Ruby' is a hybrid of the species *Bergenia cordifolia* and grows to a flowering height of 50 cm and bears deep purple-red flowers.

The only variety of *Bergenia* which is known by the inventor to be derived from the same species, *Bergenia omeiensis*, is *Bergenia* 'Apple Blossom' (U.S. Plant Pat. No. 15,101). 'Apple Blossom' is a much larger plant than 'Merry Bells'. Whereas plants of 'Apple Blossom' may reach a height of 45 cm to 60 cm and a spread of 25 cm to 50 cm, 'Merry Bells' remains no larger than 20 cm in height and 30 cm in width.

I claim:

1. A new and distinct cultivar of *Bergenia* plant named 'Merry Bells' as described and illustrated herein.

* * * * *